United States Patent
Proksa (10) Patent No.: US 11,000,238 B2
(45) Date of Patent: May 11, 2021

(54) METHOD AND DEVICE FOR DETERMINING A SPECTRAL COMPUTED TOMOGRAPHY SCAN PROTOCOL

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/611,868

(22) PCT Filed: Aug. 29, 2018

(86) PCT No.: PCT/EP2018/073172
§ 371 (c)(1),
(2) Date: Nov. 8, 2019

(87) PCT Pub. No.: WO2019/048294
PCT Pub. Date: Mar. 14, 2019

(65) Prior Publication Data
US 2020/0397387 A1 Dec. 24, 2020

(30) Foreign Application Priority Data
Sep. 8, 2017 (EP) .................................... 17190106

(51) Int. Cl.
*A61B 6/00* (2006.01)
*A61B 6/03* (2006.01)
(52) U.S. Cl.
CPC .............. *A61B 6/032* (2013.01); *A61B 6/545* (2013.01)
(58) Field of Classification Search
CPC ......... A61B 6/032; A61B 6/482; A61B 6/545; G06T 2211/408
See application file for complete search history.

(56) References Cited

U.S. PATENT DOCUMENTS

| 8,507,869 B2 | 8/2013 | Asma |
| 9,486,173 B2 | 11/2016 | Fan |

(Continued)

FOREIGN PATENT DOCUMENTS

| EP | 3375375 A1 | 9/2018 |
| JP | 2008279153 A | 11/2008 |

(Continued)

OTHER PUBLICATIONS

PCT International Search Report, International application No. PCT/EP2018/073172, dated Dec. 7, 2018.

*Primary Examiner* — Courtney D Thomas
(74) *Attorney, Agent, or Firm* — Larry Liberchuk (57) ABSTRACT

The present invention relates to a method (500) for determining a spectral scan protocol for acquiring a computed tomography (CT) image using a CT scanner and a corresponding apparatus (600). The method (500) comprises the steps of defining (510) a conventional scan protocol having scan restrictions for acquiring a conventional CT image; determining (520) a spectral scan protocol comprising a proportion of a first acquisition mode (201) and a proportion of a second acquisition mode (202), wherein the spectral scan protocol resembles the conventional scan protocol; and determining (520) the proportion of the first acquisition mode (201) and the proportion of the second acquisition mode (202) so that the scan restrictions of the conventional scan protocol are met. The method (500) and corresponding apparatus allows the determination of spectral scan protocols which reduce spectral scan mode restrictions.

12 Claims, 4 Drawing Sheets

(56) References Cited

U.S. PATENT DOCUMENTS

| 9,517,042 | B2 | 12/2016 | Hsieh |
|---|---|---|---|
| 2009/0180585 | A1 | 7/2009 | Fujimoto |
| 2010/0008472 | A1 | 1/2010 | Bohn |
| 2012/0039432 | A1 | 2/2012 | Kondo |
| 2012/0057677 | A1 | 3/2012 | Vogtmeier |
| 2015/0071400 | A1 | 3/2015 | Popescu |
| 2015/0164457 | A1 | 6/2015 | Nett |

FOREIGN PATENT DOCUMENTS

| JP | 2010167165 A | 8/2010 |
|---|---|---|
| JP | 2010284350 A | 12/2010 |
| WO | WO2016020178 A1 | 2/2016 |
| WO | WO2017027547 A1 | 2/2017 |
| WO | WO2017032864 A1 | 3/2017 |

METHOD AND DEVICE FOR DETERMINING A SPECTRAL COMPUTED TOMOGRAPHY SCAN PROTOCOL

FIELD OF THE INVENTION

The present invention relates to the field of medical imaging and in particular to a method for determining a spectral scan protocol for acquiring a computed tomography image using a computed tomography scanner and a corresponding method for acquiring a conventional computed tomography image. The invention further relates to a corresponding spectral scan protocol determination apparatus and computed tomography system. However, the present invention is not limited to the use in medical imaging and can likewise be applied in other fields.

BACKGROUND OF THE INVENTION

Dual energy or spectral computed tomography (CT) is a special imaging procedure, in which generally a plurality of CT acquisitions using at least two different X-ray beam spectra are performed. Dual energy or spectral CT allows to perform energy and/or material selective reconstruction of the patient, it is for instance possible to obtain synthetic monochromatic energy images through material decomposition.

Despite the significant advantages in evaluation capabilities, CT users regularly refrain from selecting spectral scanning and choose conventional CT acquisition instead. The main reason for the users' hesitation is that one of the two acquisition modes uses the X-ray tube power less efficiently, which can have severe impact on scan restrictions, e.g. the acquisition speed, as compared to a conventional acquisition. Accordingly, the enhanced spectral capabilities are frequently not exploited due to the scan mode restrictions of spectral CT acquisition, even in cases in which scan restrictions would allow for such spectral acquisition, and a conventional CT image is acquired instead.

SUMMARY OF THE INVENTION

It has therefore been an object of the present invention to provide a method for determining a spectral scan protocol and a method for acquiring a conventional CT image which reduce scan mode restrictions of spectral CT acquisition.

According to a first aspect a method for determining a spectral scan protocol for acquiring a computed tomography image using a computed tomography scanner is provided. The method comprises the steps of defining a conventional scan protocol having scan restrictions for acquiring a conventional CT image; determining a spectral scan protocol comprising a proportion of a first acquisition mode and a proportion of a second acquisition mode, wherein the spectral scan protocol resembles the conventional scan protocol; and determining the proportion of the first acquisition mode and the proportion of the second acquisition mode so that the scan restrictions of the conventional scan protocol are met.

In summary, the solution according to the invention thus allows the determination of a spectral scan protocol, i.e. a protocol leading to a computed tomography image having spectral resolution, while the user does not have to draw attention to the restrictions implied by defining a spectral scan protocol in the first place. According to the invention, for instance, the user can define a conventional scan protocol, i.e. a scan protocol for acquiring a conventional CT image, with the scan restrictions of the conventional scan protocol. Under consideration of these scan restrictions, which are defined for the conventional scan protocol, the method according to the invention uses possible available headroom to distribute the acquisition among a first and a second acquisition mode. Expressed differently, the method according to the present invention aims at allowing spectral acquisition without interfering with the conventional scan protocol, i.e. complies with the scan restrictions of the conventional scan protocol.

In the course of this application, a conventional scan protocol is used to refer to a protocol for obtaining a conventional CT image, i.e. a CT image for which no spectral information is acquired. Expressed differently, the term "conventional" is used to explicitly distinguish such protocol from a protocol which is defined for spectral acquisition.

In this context, it is referred to a conventional CT image as an image, which is acquired from X-ray projections at multiple angles using substantially the same X-ray spectrum, e.g. having substantially the same X-ray tube operating parameters and/or filter settings. This can for example also be expressed as an image acquisition using a single acquisition mode. In contrast thereto, spectral acquisition relies preferentially on a difference between X-ray spectra of at least two projections of the image acquisition.

The spectral scan protocol thereby resembles the conventional scan protocol. Preferentially, a CT image obtainable using the spectral scan protocol shows similar image properties, for instance in terms of image quality such as resolution, contrast, artifacts or signal-to-noise ratio. However, the spectral scan protocol will provide a CT image which further shows spectral resolution, i.e. will be enhanced compared to the conventional CT image. Further preferably, the spectral scan protocol will not lead to an increased radiation dosage on the patient as compared to the conventional scan protocol.

Preferentially, a spectral scan protocol determined by the method according to the present invention relies on a conventional scan protocol which is defined by a user in a well-known and familiar way. The determined spectral scan protocol, i.e. the enhancement based on spectral capabilities of the protocol, can then be determined by the inventive method without deteriorating the conventional scan protocol defined by the user and without further input needed by the user. The spectrally acquired CT image will then, as mentioned before, preferentially result in the same image and image quality as would have been acquired using the conventional scan protocol, yielding spectral information in addition. In summary, attractiveness of spectral acquisitions for users is increased by the method according to the invention, since restrictions of spectral scan modes are virtually reduced by entrusting the user with defining the conventional scan protocol only.

The proportion of the first acquisition mode and the proportion of the second acquisition mode is preferably to be understood as a proportion with respect to the entire scan time, respectively. Expressed differently, the proportion can refer to a single continuous time portion, i.e. the acquisition is switched from the first to the second acquisition mode once during the spectral scan. Preferably, the scan mode is switched multiple times among the first acquisition mode and the second acquisition mode during the scan, such as, for instance, in a rapid switching acquisition, and the proportion is then defined as either the relative duration of the first acquisition mode to the duration of the second acquisition mode or the sum of time periods during which the first and second acquisition mode, respectively, are used relative to the overall scan time. In many instances, both definitions would yield the same proportion, while the invention is not limited to this.

In an embodiment, the scan restrictions of the conventional scan protocol include one or more of image quality, signal-to-noise ratio, photon flux, tube power utilization, acquisition speed, and patient dose.

It should be noted that some protocol or scan restrictions are mutually dependent, such as image quality and signal-to-noise ratio or also photon flux and tube power utilization. Particularly, scan speed or acquisition speed has shown to be a limiting factor for the use of spectral CT acquisition. Using the method according to the invention, a spectral acquisition is possible while, for instance, scan or acquisition speed requirements are met. It should be noted that these scan restrictions are examples and in other embodiments additional or alternative scan restrictions can be defined.

In an embodiment the first acquisition mode and the second acquisition mode correspond to one or more of different X-ray tube voltages and a different beam filtration.

Preferably, spectral CT imaging techniques perform rapid spectral switching to change the spectral properties of the image acquisition between the first acquisition mode and the second acquisition mode. One example of switching X-ray tube voltages among acquisition modes is known as kVp switching in literature. Switching the X-ray tube voltage has a direct influence on the X-ray beam spectrum, such that two image acquisitions using the different X-ray tube voltages carry spectral information. Likewise, a different beam filtration among the first acquisition mode and the second acquisition mode results in two different X-ray spectra, respectively. It should be noted that in some embodiments also more than two different acquisition modes or also further forms of providing alternating X-ray beam spectra are contemplated.

In an embodiment the second acquisition mode uses a power of an X-ray tube of the computed tomography scanner less efficiently than the first acquisition mode.

For instance with respect to the different acquisition modes exemplified above, a low X-ray tube voltage will generate less X-ray flux and thus lead to a lower X-ray tube power utilization or, expressed differently, a less efficient power use. Likewise, using a filter for filtering the X-ray beam will reduce the X-ray flux as compared to a non-filtered use. While in this embodiment the second acquisition mode is defined as the one out of both acquisition modes having the less efficient X-ray tube power utilization, the choice is of course arbitrary. In general, one acquisition mode out of a first acquisition mode and a second acquisition mode will be less efficient, which is just referred to as the second acquisition mode in this embodiment. Due to the less efficient power utilization, significant restrictions, for instance to the scan or acquisition speed, can be the result. In response, the method according to the invention avoids interference with scan protocol restrictions by adjusting or determining the proportions of the first and second acquisition mode accordingly.

In an embodiment, the method further comprises the steps of: determining a tube power utilization percentage necessary to fulfill the scan restrictions of the conventional scan protocol and determining the proportion of the first acquisition mode and the proportion of the second acquisition mode to meet the required tube power utilization percentage.

Preferably, the tube power utilization percentage is defined as the ratio of useful X-ray energy, i.e. the flux detectable at the detector, compared to the power the X-ray tube is operated with. Preferably, the necessary tube power utilization percentage is determined as the minimum tube power utilization, i.e. using the maximum tube power, which has minimally to be complied with in order to fulfill the scan restrictions. Using the tube power with a percentage, which would be below this minimum determined percentage, would lead to a too noisy image, since not enough X-ray photons would arrive at the detector. As described above, one of the two acquisition modes, exemplarily the second acquisition mode, uses the X-ray tube power less efficiently. However, if the tube power utilization percentage for maximum tube power is below the tube power utilization percentage acquired by purely using the first acquisition mode, the required minimum tube power utilization percentage will still be achieved in case a proportion of the acquisition is done using the second acquisition mode, i.e. the acquisition mode having a lower tube power utilization percentage. It should be noted that instead of tube power utilization, also other parameters can be determined for deriving a head room capacity of a scan protocol.

In an embodiment, the method further comprises the step of optimizing the proportion of the first acquisition mode and the proportion of the second acquisition mode in terms of spectral capabilities.

The spectral capability can, for instance, be defined as the capability for the decomposition of tissue. For instance, a signal-to-noise ratio of the acquired image can be taken as an indicator for the spectral capabilities, while the invention is not limited to this. Preferentially, in this embodiment the spectral capabilities of the acquisition are thus optimized, while at the same time the scan requirements of the conventional scan protocol are not infringed. Preferably, the optimum proportions in terms of spectral capabilities correspond to proportions, in which the total dose for both acquisitions would approximately be the same.

In an embodiment, the method further comprises the steps of determining optimum proportions as the proportion of the first acquisition mode and the proportion of the second acquisition mode point with optimum spectral capabilities, and, in case the spectral scan protocol using the optimum proportions meets the scan restrictions, determining the proportion of the first acquisition mode and the proportion of the second acquisition mode, respectively, as the optimum proportions.

Both an acquisition with the first acquisition mode or the second acquisition mode only will not lead to spectral capability at all. It is thus obvious that the point of maximum or optimum spectral capabilities has to be somewhere in between these boundaries. For instance, the optimum spectral capabilities point can be derived from determining a maximum of a signal-to-noise ratio as a function of the relative acquisition time in the first acquisition mode and in the second acquisition mode. However, of course other alternatives for determining the point with optimum spectral capabilities are contemplated.

In case the point of optimum spectral capabilities is reachable without infringing the scan protocol restrictions, e.g. in terms of tube power utilization, scanning time and the like, the proportions leading to the optimum spectral capabilities point can directly be used as the proportion of the first acquisition mode and the second acquisition mode, respectively. Accordingly, the head room in this instance is large enough to accommodate the additional power requirement for spectral acquisition. Expressed even differently, a spectral acquisition can be feasible by only increasing the tube power to account for the less efficient acquisition mode, without further impact on the protocol restrictions.

In an embodiment, the method further comprises, in case the spectral scan protocol using the optimum proportions does not meet the scan restrictions, the step of increasing, starting from the optimum proportions, the proportion of the one of the first acquisition mode and the second acquisition mode having a higher X-ray tube utilization until the scan restrictions are met.

In this embodiment, the point with optimal spectral capabilities is not accessible without having impact on the scan restrictions. Accordingly, spectral acquisition with optimum spectral performance is not able to be carried out without, for instance, increasing the scan time. But, instead of not using spectral detection at all, according to this embodiment the proportions of the respective acquisition modes are determined so as to provide the best spectral capabilities without having impact on the conventional scan protocol. Thus, while the spectral acquisition is not perfect, it will still provide valuable information enhancing the conventional scan.

According to a further aspect, a method of acquiring a conventional CT image using a CT scanner is provided. The method comprises the steps of: determining a spectral scan protocol according to the first aspect of the invention, performing spectral acquisition using the determined spectral scan protocol, and fusing the spectrally acquired data to a conventional CT image.

According to this method, a conventional CT image can be obtained, using the conventional scan protocol in a classical way. However, due to the additional spectral acquisition integrated through the determined spectral scan protocol, spectral information is available additionally and can be used to improve the evaluation of the CT data. Accordingly, the user can later decide whether to use the additional spectral information for evaluation or not. Yet, at the time of defining the scan protocol, the user only has to define the conventional scan protocol as he or she is used to. In case the system resources allow a spectral acquisition, data will be acquired spectrally, even without the user having to specifically designate spectral acquisition. The method according to this aspect can of course also be advantageously combined with any of the embodiments described with respect to the first aspect described above.

According to a further aspect a spectral scan protocol determination apparatus for determining a spectral scan protocol for acquiring a computed tomography image using a computed tomography scanner is provided. The apparatus comprises a conventional scan protocol providing unit for defining a conventional scan protocol having scan restrictions, the conventional scan protocol describing an acquisition of a conventional computed tomography image, a spectral scan protocol determination unit for determining a spectral scan protocol comprising a proportion of a first acquisition mode and a proportion of a second acquisition mode, wherein the spectral scan protocol resembles the conventional scan protocol, and a proportion determination unit for determining the proportion of the first acquisition mode and the proportion of the second acquisition mode so that the scan restrictions of the conventional scan protocol are met.

The apparatus according to this aspect allows to determine a spectral scan protocol based on the scan mode restrictions of a conventional scan protocol, and thus with reduced scan mode restrictions compared to a typical spectral scan protocol definition. The apparatus can achieve the same improvements and advantages over the prior art as the method according to the first aspect and can further advantageously be combined with any of the embodiments described above with respect to the first aspect.

According to a further aspect, a CT system is provided. The CT system comprises an apparatus for determining a spectral scan protocol according to an aspect of the present invention, and a CT scanner, wherein the CT scanner is configured to perform spectral acquisition using the determined spectral scan protocol and to fuse the spectrally acquired data to a conventional CT image.

The system allows to determine a conventional CT image in a conventional way, in which the user defines a conventional CT scan having conventional scan mode restrictions. Yet, as a result of the invention, unused capacities or resources of the CT scanner are advantageously used to enhance the conventional CT image using spectral acquisition. Thus, a user only is required to define the conventional CT scan in a well-known way, while the burden of complying with spectral scan mode restrictions is taken away by the system according to the invention.

In a further aspect a computer program for determining a spectral scan protocol for acquiring a computed tomography image using a computed tomography scanner is provided. The computer program comprises program code means for causing an apparatus as defined in claim 10 to carry out the method as defined in claim 1, when the computer program is run on the apparatus.

It shall be understood that the method for determining a spectral scan protocol of claim 1, the method of acquiring a conventional computed tomography image of claim 9, the spectral scan protocol determination apparatus of claim 10, the computed tomography system of claim 11 and the computer program of claim 12 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
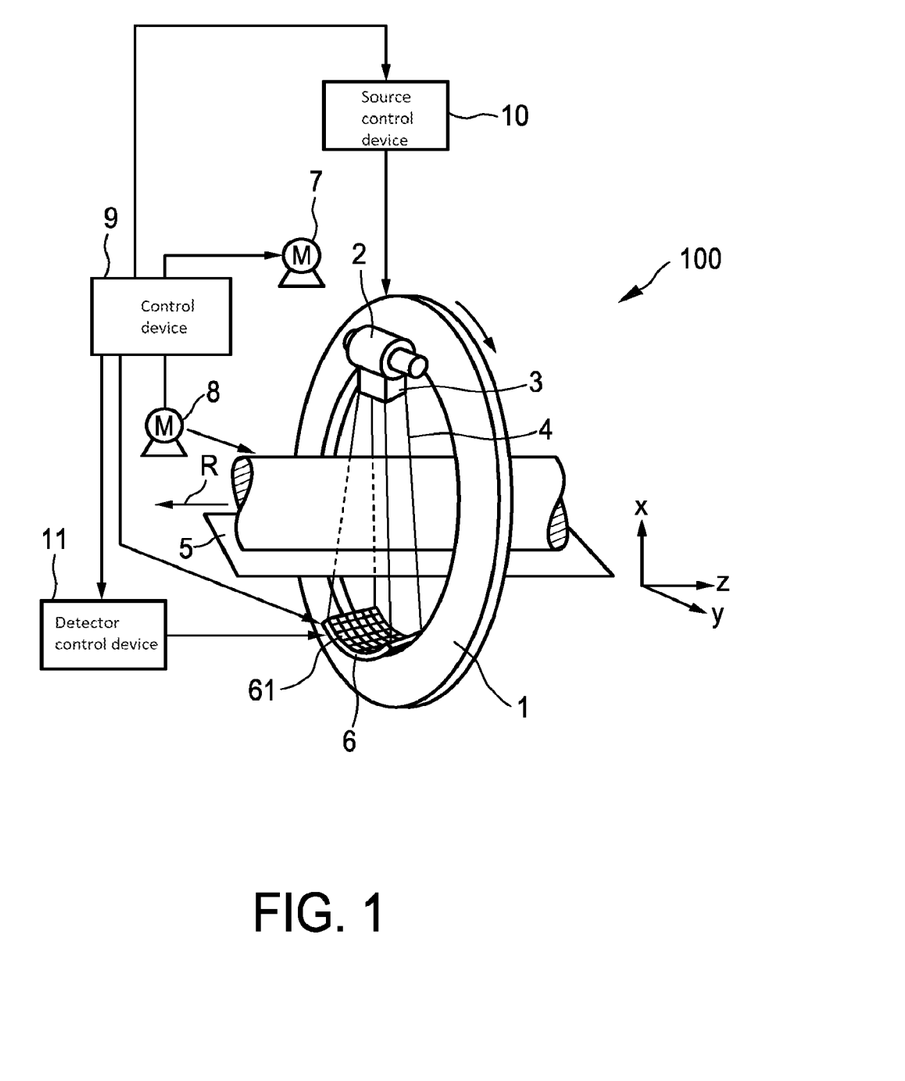
FIG. 1 schematically and exemplarily shows a CT scanning system.

FIG. 1 shows an example of a CT imaging system 100 for medical applications and examination of a patient that can be used with the methods and apparatus according to the invention. The CT imaging system 100 shown in FIG. 1 includes a gantry 1 which is capable of rotation about an axis of rotation R which extends parallel to the z direction. The radiation source 2, in particular a conventional X-ray tube, for instance with rotating tungsten anode is mounted on the gantry 1. The X-ray tube 2 is provided with a collimator device 3 which forms a shaped radiation beam 4, such as a fan, cone wedge or any other predetermined shape, from the radiation produced by the X-ray tube 2. The radiation traverses an object (not shown), such as a patient positioned on a support 5, in a region of interest in a cylindrical examination zone (imaging region). After having traversed the examination zone, the X-ray beam 4 is incident on an X-ray detector unit 6, in this embodiment a two-dimensional photon-counting detector having a plurality of detector cells 61, which is mounted on the gantry 1 and which converts incident X-ray radiation into detection signals.

The gantry 1 is driven at a preferably constant but adjustable angular speed by a motor 7. A further motor 8 is provided for displacing the object, e.g. the patient who is arranged on a patient table in the examination zone, i.e. support 5, parallel to the direction of the axis of rotation R or the z axis as indicted in FIG. 1. These motors 7, 8 are controlled by a control device 9, for instance such that the radiation source 2 and the examination zone 5 move relative to one another along a helical trajectory. However, it is also possible that the object or the support 5 is not moved, but that only the X-ray source 2 is rotated.

When performing the actual scan, the control device 9 provides respective commands to the motors 7 and 8 to position the support 5 and rotate the gantry 1 around the examination zone. For predetermined positions, the control device 9 issues operation commands to the source control device 10 that initiate the corresponding emission of a radiation beam 4 by the X-ray source 2 for a time period corresponding to the predetermined pulse width. The control device 9 can simultaneously issue respective commands to a detector control device 11 that initiates operation of the photon detector 6 with a predetermined delay, e.g. 1-3 µsec, compared to the initiation of the X-ray source 2. Furthermore, the detector control device 11 can stop operation of the photon detector 6 after the time period corresponding to the predetermined pulse width has been reached, e.g. the detector 6 stops operation together with or even slightly before the X-ray source 2.

The CT imaging system 100 shown in FIG. 1 is configured for spectral image acquisition. In the following, rapid spectral switching to change the spectral properties of the image acquisition from projection to projection is described as an example of the spectral image acquisition, while also other known examples of spectral image acquisition for CT applications are likewise contemplated.

In this example, source control device 10 controls X-ray source 2 or, alternatively or additionally, collimator device 3 to switch between a first acquisition mode and a second acquisition mode. Expressed differently, either the X-ray tube voltage of X-ray source 2 or beam filtration using collimator device 3, for instance, can be switched among the two acquisition modes. In both cases one of the two acquisitions uses the power of X-ray source 2 less efficiently. For instance, in kVp switching, the low kVp setting will generate less X-ray flux. In order to compensate for this effect and optimize spectral separation, the acquisition time of the acquisition mode with lower kVp setting can be extended to obtain roughly the same total dose for both settings. This, however, limits the effective overall tube power utilization and can have impact on scan speed and other protocol restrictions. In filter switching approaches, the filter may significantly reduce the flux and, similar to the kVp switching, non-equidistant acquisition times or proportions of the first and second acquisition mode may compensate for these effects on the spectral separation. The invention now addresses the aspect of protocol restrictions by adjusting the relative timing of the first and second acquisition mode to provide as much spectral resolution as possible, without infringing or having impact on the conventionally defined scan protocol.

Figure 2:
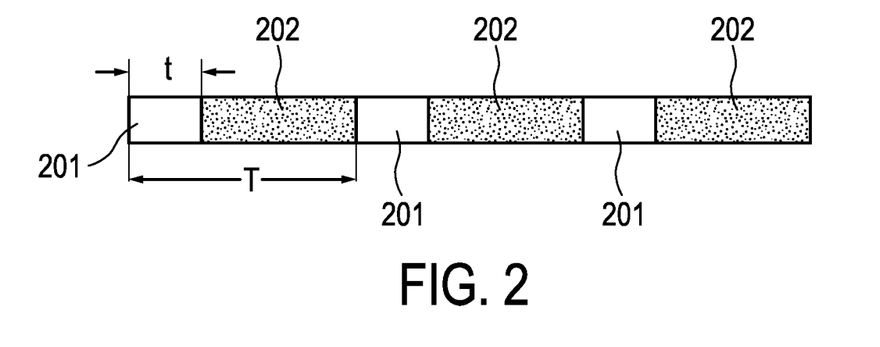
FIG. 2 schematically and exemplarily shows a timing of proportional acquisition using two acquisition modes.

FIG. 2 schematically and exemplarily shows a relative timing of proportional acquisition using two acquisition modes 201, 202. Two successive acquisitions using a first acquisition mode 201 and a second acquisition mode 202 sum up to a total time T. A plurality of these successive acquisitions 201, 202 will result in the complete scan.

A time period t is defined as the proportion of acquisition mode 201 to the time duration of two successive acquisitions 201 and 202, i.e. T. If t=0, only the second acquisition mode 202 would be used for acquisition. At t=T/2 or t/T=0.5, both acquisition modes 201, 202 would contribute with half of the total acquisition time each. Finally, if t=T, acquisition would only be performed using first acquisition mode 201. For completeness, in this example the proportion of acquisition mode 202 could easily be expressed as the proportion of T−t to T.

In case t would be determined so that the total dose for both acquisitions would roughly be the same (or spectral separation would be at its maximum), possible side effects on protocol restrictions, such as scan speed, can occur. It is a finding of the present invention that the proportions of both acquisition modes 201, 202 be determined differently, namely with a focus on the scan restrictions, such that the user does not have to adapt his or her conventionally defined scan protocol, but can use the conventional scan protocol having conventional scan mode restrictions using a spectrally enhanced acquisition.

Figure 3:
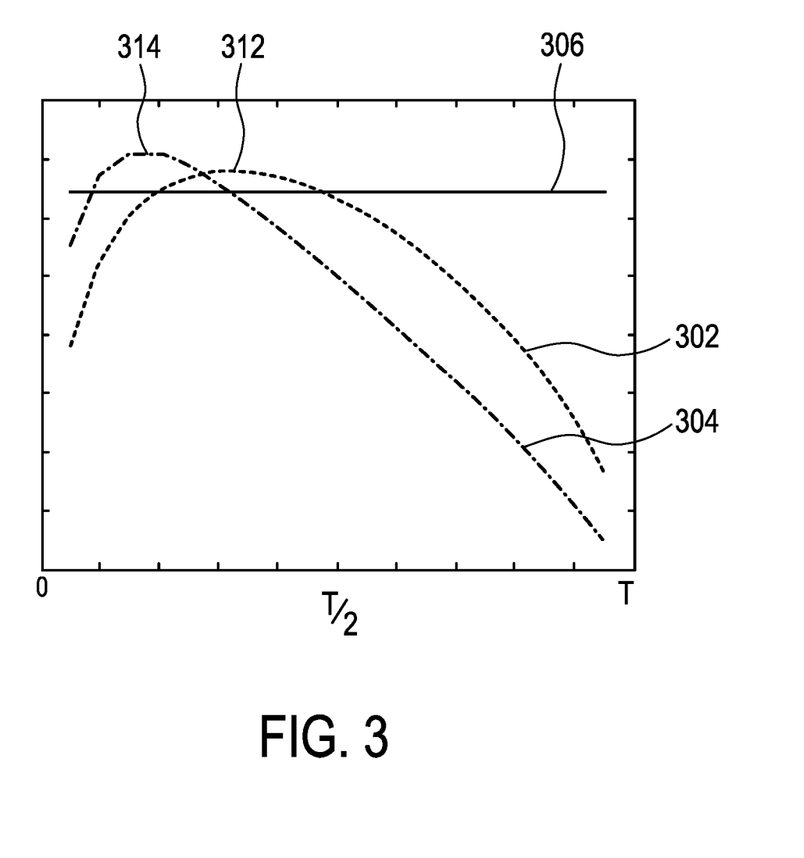
FIG. 3 schematically and exemplarily shows a curve indicating a typical signal-to-noise ratio over the proportion of relative acquisition in the two acquisition modes.

FIG. 3 schematically and exemplarily shows the change of an image quality measure, e.g. a signal-to-noise ratio, on the vertical axis over the proportion t of the first acquisition mode 201 relative to two successive acquisitions T of the first and second acquisition mode 201 and 202. A curve 302 indicates, for instance, an absolute signal-to-noise ratio which has a maximum 312 somewhere below T/2, i.e. with the first acquisition mode 201 having a lower proportion than the second acquisition mode 202.

Whenever possible, acquisition should be done at the peak of this curve. Expressed differently, in some examples, the maximum 312 would be determined as the optimum proportion of first acquisition mode 201 and second acquisition mode 202. Further, FIG. 3 illustrates an additional curve 304, which in this example relates to a dose normalized signal-to-noise ratio having a maximum 314 at an even lower proportion of first acquisition mode 201 than maximum point 312. Depending on the application, one or the other measure for determining the optimum proportions between first and second acquisition mode 201, 202, can be used.

For reference, a line 306 indicates a signal-to-noise ratio using a dual layer detector, i.e. a detector which always acquires scans with spectral information, which means that there is no special acquisition mode that needs to be switched on and for all acquisitions it can later be decided whether or not to reduce the spectral results. However, spectral detectors are not always accessible, and spectral acquisitions using the present invention can also be carried out using spectral CT scanners not having dual layer or spectral detectors.

Figure 4:
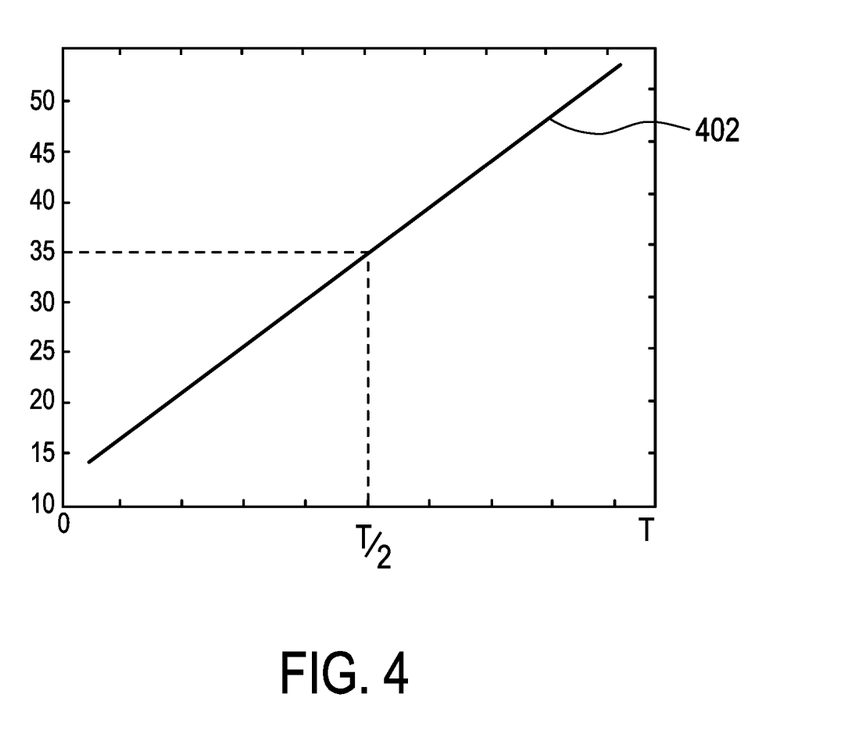
FIG. 4 schematically and exemplarily shows a curve indicating a typical tube power utilization ratio over the proportion of relative acquisition in the two acquisition modes.

FIG. 4 schematically and exemplarily shows a curve 402 indicating a typical tube power utilization ratio in exemplary percentage values on the vertical axis over the same relative acquisition time on the horizontal axis as shown in FIG. 3. Curve 402 is drawn linear in this example, while also deviant dependencies of the tube power utilization with relative acquisition time are possible. As can be seen, the tube power utilization increases with the relative proportion of acquisition in the first acquisition mode 201, i.e. with t approaching T. Spectral performance is generally maximum in case the signal-to-noise ratio is approximately equal in both acquisitions, i.e. the same for the acquisition using first acquisition mode 201 and the acquisition using second acquisition mode 202.

Upon combining FIGS. 3 and 4, it can be seen that the peak values 312 or 314 correspond to a rather low tube power utilization on curve 402. Expressed differently, in case an acquisition is to be performed using the relative proportions which correspond to peak 312 or 314, respectively, it is likely to interfere with scan mode restrictions, such as scan speed, due to the low tube power utilization at these proportions. It is now key of the present invention to determine the proportion of the first acquisition mode 201 and the second acquisition mode 202 so that the tube power utilization, for instance, complies with the scan mode requirements.

More specifically, for instance in case the peak values 312 or 314 would impose protocol restrictions, the proportions will be determined more on the right of FIG. 3 or FIG. 4, i.e. with a higher proportion of the first acquisition mode 201, so that protocol restrictions are met.

Just to give some non-limiting examples, in case the required tube power utilization would only be 15%, selecting the peak values 312 or 314 would not impose a problem on the protocol and thus spectral acquisition can be carried out without implications using the proportions corresponding to peak values 312 or 314 due to the available additional power capacity.

However, in case the protocol's required tube power utilization would be 35%, an acquisition using the proportions that would yield the maximum image quality, i.e. peak value 312 or 314, would not be possible due to the too low tube power utilization. Referring to FIG. 4, some spectral scanning is nevertheless possible, in this example using t=T/2 or equal proportions of the first and second acquisition mode 201, 202. Yet, while this acquisition will not provide optimum spectral separation or spectral results, it will still enhance the conventional image with the additional spectral information due to the acquisition using two different acquisition modes. At the same time, the protocol restrictions of the conventional scan protocol are always met.

Figure 5:
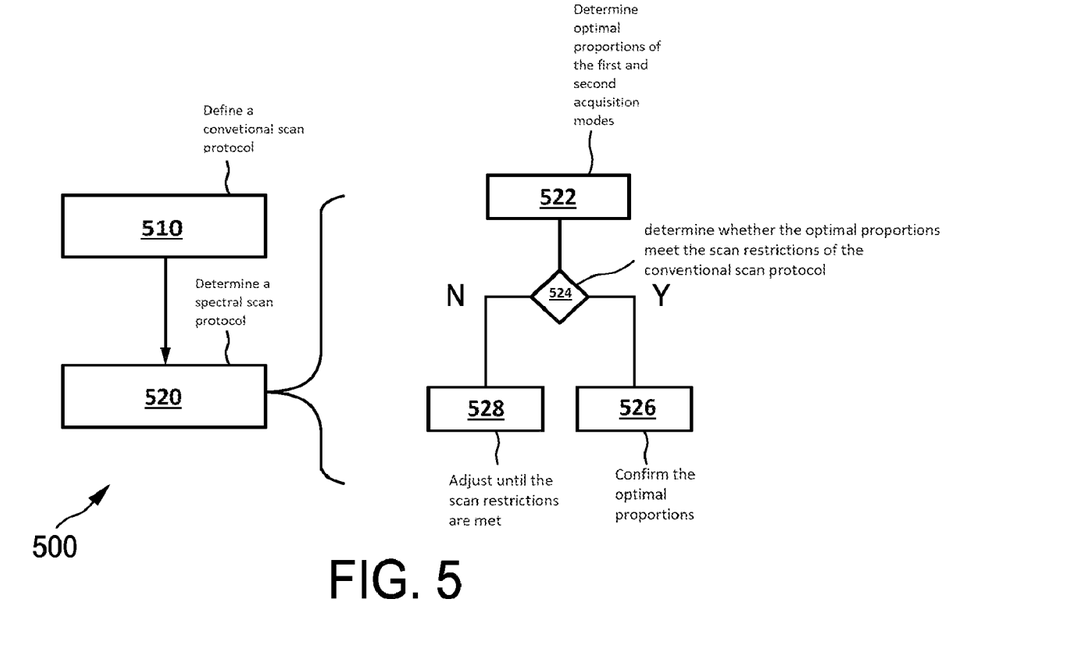
FIG. 5 schematically and exemplarily illustrates a flowchart of a method for determining a spectral scan protocol according to the invention.

FIG. 5 will schematically and exemplarily illustrate a flowchart of a method 500 for determining a spectral scan protocol according to the invention.

In a first step 510, the method comprises defining of a conventional scan protocol having scan restrictions for acquiring a conventional CT image. The conventional scan protocol is a protocol for which spectral acquisition has not been activated by the user. Expressed differently, the user is familiar with the definition of the conventional scan protocol and does not have to deal with spectral scan mode restrictions.

In a step 520, based on the conventional scan protocol, a spectral scan protocol is determined. The spectral scan protocol comprises a proportion of a first acquisition mode 201 and a second acquisition mode 202, wherein the spectral scan protocol resembles the conventional scan protocol.

In step 520, the proportion of the first acquisition mode 201 and the second acquisition mode 202 are determined in a particular way which is so that the scan restrictions of the conventional scan protocol are met. Contrary to previously known methods for acquiring spectral scan protocols, in which scan or protocol restrictions were imposed based on the determined proportions, according to the invention the restrictions of the protocol are first determined and the proportions of the first and second acquisition mode, respectively, are then determined based on the provided scan restrictions in a second stage. This means that the spectral acquisition does not impose scan mode restrictions on the user, to whom the attractiveness of spectral acquisitions is thus increased.

Step 520 can in one example comprise multiple substeps which will be discussed in the following. Step 520 comprises substeps 522 to 528 in this example. First, in a step 522, optimal proportions of the first acquisition mode 201 and the second acquisition mode 202 at which the acquisition has optimum spectral capabilities are determined. In one example, optimum spectral capabilities are present in case the signal-to-noise ratio is equal for both the acquisition in the first acquisition mode 201 and the second acquisition mode 202.

Next, in a step 524, it is decided whether the optimum proportions meet the scan restrictions of the conventional scan protocol defined in step 510. Whether the optimum proportions meet the scan restrictions can be determined by, for instance, evaluating a protocol required beam power utilization percentage, which is required to meet the scan restrictions, with a possible beam power utilization percentage, which would be possible using an acquisition with the determined optimum proportions.

In case the acquisition using the determined optimum proportions meets the conventional scan requirements, in a step 526 the proportions of the first acquisition mode 201 and the second acquisition mode 202 are determined as the respective optimum proportions determined in step 522.

In case the optimum proportions determined in step 522 do not meet the scan restrictions, in step 528 it is deviated from the optimum proportions until the scan restrictions are met. Specifically, in one example the proportion of the one of the first acquisition mode 201 and the second acquisition mode 202 having a higher X-ray tube utilization is increased until the scan restrictions are met. Thus, after step 520, exemplarily after step 528 or 526 in the exemplary embodiment of step 520, proportions of the first acquisition mode 201 and the second acquisition mode 202, respectively, are determined which in combination allow a spectral scan protocol that meets the scan requirements of the conventional scan protocol.

The spectral scan protocol determined as a result of method 500 can, in one example, be used for acquiring a conventional CT image, wherein spectral acquisition using this determined spectral scan protocol is performed and the spectrally acquired data is, in a later step, fused to a conventional CT image. In addition, the enhanced spectrally resolved data can be used for further evaluation of the scanned tissue, for instance.

Figure 6:
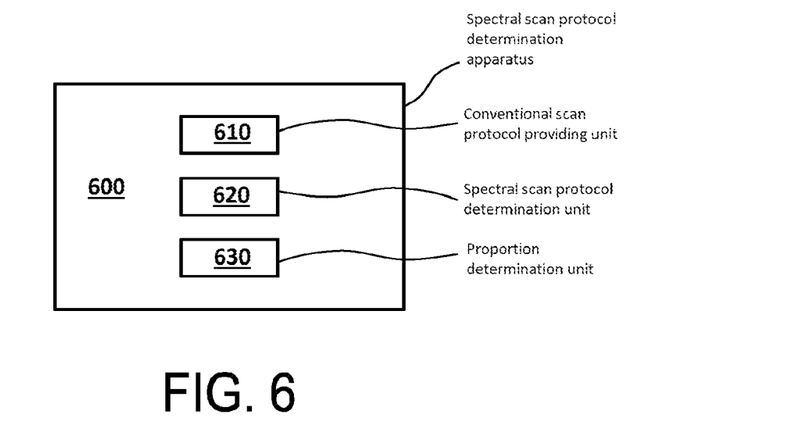
FIG. 6 schematically and exemplarily illustrates a spectral scan protocol determination apparatus according to the invention.

Finally, FIG. 6 schematically and exemplarily illustrates a spectral scan protocol determination apparatus 600 according to the invention. Spectral scan protocol determination apparatus 600 is configured to determine a spectral scan protocol, for instance in accordance with method 500 described above, for acquiring a CT image using a CT scanner, such as a CT scanner of computed tomography system 100. Apparatus 600 comprises a conventional scan protocol providing unit 610, a spectral scan protocol determination unit 620 and a proportion determination unit 630.

Apparatus 600 can in its entirety or partly be implemented as processing means, for instance general purpose processing units as known in the art. In one example, apparatus 600 can be integrated into control device 9 as illustrated in FIG. 1. Each of conventional scan protocol providing unit 610, spectral scan protocol determination unit 620 and proportion determination unit 630 can likewise be implemented as part of the processor forming apparatus 600 or as separate and respectively interconnected and communicating processing units. One, more or all of the elements can of course also be implemented on distributed computing devices, for instance on servers, and communicate via a network, such as the Internet.

Conventional scan protocol providing unit 610 is configured to define a conventional scan protocol having scan restrictions, wherein the conventional scan protocol describes an acquisition of a conventional CT image.

Spectral scan protocol determination unit 620 is configured to determine a spectral scan protocol comprising a proportion of a first acquisition mode 201 as shown in FIG. 2 and a proportion of a second acquisition mode 202, wherein the spectral scan protocol resembles the conventional scan protocol.

Finally, proportion determination unit 630 is configured to determine the proportion of the first acquisition mode 201 and the proportion of the second acquisition mode 202, so that the scan restrictions of the conventional scan protocol are met. Spectral scan protocol determination apparatus 600 thus allows the user to spectrally acquire an image without having to particularly worry about scan mode restrictions of a spectral scan. Thus, the attractiveness of spectral acquisitions is increased through the use of spectral scan protocol determination apparatus 600.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for determining a spectral scan protocol for acquiring a computed tomography image using a computed tomography scanner, the method comprising:
    defining a conventional scan protocol having scan restrictions for acquiring a conventional computed tomography image,
    determining a spectral scan protocol comprising a proportion of a first acquisition mode and a proportion of a second acquisition mode, wherein the spectral scan protocol resembles the conventional scan protocol, and
    determining the proportion of the first acquisition mode and the proportion of the second acquisition mode so that the scan restrictions of the conventional scan protocol are met.

2. The method according to claim 1, wherein the scan restrictions of the conventional scan protocol include at least one of image quality, signal-to-noise ratio, photon flux, tube power utilization, acquisition speed, and patient dose.

3. The method according to claim 1, wherein the first acquisition mode and the second acquisition mode correspond to at least one of different X-ray tube voltages and a different beam filtration.

4. The method according to claim 1, wherein the second acquisition mode uses a power of an X-ray tube of the computed tomography scanner less efficiently than the first acquisition mode.

5. The method according to claim 1, further comprising:
    determining a tube power utilization percentage necessary to fulfil the scan restrictions of the conventional scan protocol; and
    determining the proportion of the first acquisition mode and the proportion of the second acquisition mode to meet the required tube power utilization percentage.

6. The method according to claim 1, further comprising:
    optimizing the proportion of the first acquisition mode and the proportion of the second acquisition mode in terms of spectral capabilities.

7. The method according to claim 1, further comprising:
    determining optimum proportions as the proportion of the first acquisition mode and the proportion of the second acquisition mode with optimum spectral capabilities, and
    if the spectral scan protocol using the optimum proportions meets the scan restrictions, determining the proportion of the first acquisition mode and the proportion of the second acquisition mode, respectively, as the optimum proportions.

8. The method according to claim 7, further comprising, if the spectral scan protocol using the optimum proportions does not meet the scan restrictions:
    increasing, starting from the optimum proportions, the proportion of the one of the first acquisition mode and the second acquisition mode having a higher X-ray tube utilization until the scan restrictions are met.

9. A method of acquiring a conventional computed tomography image using a computed tomography scanner, the method comprising:
    determining a spectral scan protocol according to claim 1,
    performing spectral acquisition using the determined spectral scan protocol, and
    fusing the spectrally acquired data to a conventional computed tomography image.

10. A non-transitory computer readable medium having stored thereon a computer program for determining a spectral scan protocol for acquiring a computer tomography image, the computer program causing an apparatus to carry out a method according to claim 1.

11. A spectral scan protocol determination apparatus for determining a spectral scan protocol for acquiring a computed tomography image using a computed tomography scanner, the apparatus comprising:
    a digital storage memory configured to store processor executable instructions; and at least one processor configured to execute the processor executable instructions to:
- define a conventional scan protocol having scan restrictions, the conventional scan protocol describing an acquisition of a conventional computed tomography image;
- determine a spectral scan protocol comprising a proportion of a first acquisition mode and a proportion of a second acquisition mode, wherein the spectral scan protocol resembles the conventional scan protocol; and
- determine the proportion of the first acquisition mode and the proportion of the second acquisition mode so that the scan restrictions of the conventional scan protocol are met.

12. A computed tomography system, comprising an apparatus for determining a spectral scan protocol according to claim 11, and a computed tomography scanner configured to perform spectral acquisition using the determined spectral scan protocol and to fuse the spectrally acquired data to a conventional computed tomography image.

* * * * *